(12) United States Patent
Durham et al.

(10) Patent No.: US 9,040,023 B2
(45) Date of Patent: May 26, 2015

(54) METHOD OF TREATING A MAMMALIAN TEAT AND RELATED COMPOSITIONS

(75) Inventors: Carmine J. Durham, Madison, WI (US); Michael C. Pawlak, Middleton, WI (US); Randal D. Stevenson, Cottage Grove, WI (US)

(73) Assignee: Zurex PharmaAgra, Middleton, WI (US)

( * ) Notice: Subject to any disclaimer, the term of this patent is extended or adjusted under 35 U.S.C. 154(b) by 0 days.

(21) Appl. No.: 13/481,537

(22) Filed: May 25, 2012

(65) Prior Publication Data

US 2012/0301407 A1 Nov. 29, 2012

Related U.S. Application Data

(60) Provisional application No. 61/491,053, filed on May 27, 2011.

(51) Int. Cl.
| | | |
|---|---|---|
| *A61K 31/235* | (2006.01) | |
| *A61K 9/00* | (2006.01) | |
| *A61K 47/02* | (2006.01) | |
| *A61K 47/10* | (2006.01) | |
| *A61K 9/06* | (2006.01) | |
| *A61K 47/32* | (2006.01) | |
| *A61K 9/08* | (2006.01) | |
| *A61K 31/194* | (2006.01) | |
| *A61K 31/5415* | (2006.01) | |
| *A61K 47/36* | (2006.01) | |
| *A61K 47/38* | (2006.01) | |

(52) U.S. Cl.
CPC ........... *A61K 31/235* (2013.01); *A61K 2800/42* (2013.01); *A61K 9/0041* (2013.01); *A61K 47/02* (2013.01); *A61K 47/10* (2013.01); *A61K 9/06* (2013.01); *A61K 47/32* (2013.01); *A61K 9/08* (2013.01); *A61K 47/36* (2013.01); *A61K 47/38* (2013.01); *A61K 31/194* (2013.01); *A61K 31/5415* (2013.01)

(58) Field of Classification Search
None
See application file for complete search history.

(56) References Cited

U.S. PATENT DOCUMENTS

| | | | |
|---|---|---|---|
| 4,022,199 A * | 5/1977 | Fetty | 604/290 |
| 6,749,869 B1 | 6/2004 | Richter et al. | |
| 2003/0206971 A1 | 11/2003 | McSherry et al. | |
| 2009/0110754 A1 * | 4/2009 | Stevenson | 424/663 |
| 2009/0291944 A1 * | 11/2009 | Ash et al. | 514/227.5 |
| 2010/0010086 A1 | 1/2010 | Ash et al. | |

FOREIGN PATENT DOCUMENTS

| | | |
|---|---|---|
| RU | 2262699 C2 * | 10/2005 |
| WO | WO 9913892 A1 * | 3/1999 |
| WO | WO 02/35931 A1 | 5/2002 |
| WO | WO 2006/085840 A1 | 8/2006 |
| WO | WO 2011/069974 A2 | 6/2011 |

OTHER PUBLICATIONS

Keefe, G.P.," *Streptococcus agalactiae mastitis*: a review", Can Vet J., Jul. 1997, 38(7), pp. 429-437.*
International Search Report and Written Opinion for PCT/US2012/039707 mailed Oct. 30, 2012 (14 pages).
International Search Report and Written Opinion for PCT/US2012/039707 mailed Dec. 8, 2014 (14 pages).

* cited by examiner

*Primary Examiner* — Carlos Azpuru
*Assistant Examiner* — Casey Hagopian
(74) *Attorney, Agent, or Firm* — Leydig, Voit & Mayer, Ltd.

(57) ABSTRACT

A method of treating or protecting a mammalian teat by applying a topical composition to the teat, wherein the topical conditioning composition comprises (a) citrate; (b) methylene blue; and (c) an alkyl para-hydroxybenzoate; as well as related methods and compositions.

19 Claims, No Drawings

METHOD OF TREATING A MAMMALIAN TEAT AND RELATED COMPOSITIONS

CROSS REFERENCE TO RELATED APPLICATIONS

This application claims priority to U.S. Provisional Patent Application No. 61/491,053 filed on May 27, 2011.

BACKGROUND OF THE INVENTION

Care and maintenance of the teats and udders of dairy animals is essential in order to prevent damage to the animals and economic loss to the dairy farmer. Infections of the teats of dairy animals, such as mastitis, can result in increased veterinary costs, loss of milk production, and, in serious cases, death of the dairy animal. One approach to caring for the teats and udders of dairy animals is the application of topical compositions to the teats and udders in order to maintain skin quality and reduce infections. However, there continues to be a need for new, effective methods and compositions useful for this purpose.

BRIEF SUMMARY OF THE INVENTION

Provided herein is a method of treating or protecting a mammalian teat. According to one aspect, the method comprises applying a topical composition to the teat, wherein the topical composition comprises (a) citrate; (b) methylene blue; and (c) an alkyl para-hydroxybenzoate. According to another aspect, the method comprises applying to the teat a first topical composition comprising a polymer, and a second topical composition comprising a cross-linking agent for the polymer, whereby a protective coating is provided on the teat. The first or second compositions, or both, optionally further comprise citrate, methylene blue, or alkyl para-hydroxybenzoate.

Compositions useful in the above methods, or for other purposes, also are provided herein. In one aspect, a composition is provided, which comprises (a) about 0.1-2 M citrate; (b) about 0.1-1 mM methylene blue; (c) about 10-50 mM alkyl para-hydroxybenzoate; (d) about 0.1% to about 20% alcohol; and (e) about 5 wt. % or more emollient. In another aspect, a composition is provided that comprises (a) about 0.1-2 M citrate; (b) about 0.1-1 mM methylene blue; (c) about 10-50 mM alkyl para-hydroxybenzoate; (d) about 20% to about 80% alcohol; and (e) a gelling agent. Also, compositions intended for sequential or simultaneous use are provided, as well as a kit comprising the individual compositions, is provided herein. One such composition comprises (a) citrate; (b) about 0.1-1 mM methylene blue; and (c) about 5-50 wt. % polymer. Another such composition comprises (a) about 0.1-2 M citrate; (b) about 20-100 mM alkyl para-hydroxybenzoate; (c) about 1-10% alcohol; and (d) a cross-linking agent.

DETAILED DESCRIPTION OF THE INVENTION

Provided herein is a method of treating or protecting a mammalian teat by applying particular topical compositions to the teat. By "treat or protect," it is meant that the composition once applied maintains or improves the health or condition of the teat, specifically the health or condition of the skin of the teat. Without intending to limit the scope of the subject matter described herein to any particular theory or mechanism of action, it is believed the topical compositions described herein treat or protect the skin of the teat as a result of the antimicrobial properties of the composition, the emollient or protective barrier-forming properties of the composition, or some combination thereof.

According to one aspect, the topical composition comprises (a) citrate; (b) methylene blue; and (c) an alkyl para-hydroxybenzoate. Any suitable amount of citrate, methylene blue, and alkyl para-hydroxybenzoate can be used, provided the composition retains the ability to treat or protect a mammalian teat. Without wishing to be bound by any particular theory, it is believed that the citrate, methylene blue, and alkyl-hydroxybenzoate together provide an enhanced antimicrobial effect. Thus, in one embodiment, the composition comprises each of these components in a concentration sufficient to exert an antimicrobial effect.

The methylene blue provides the additional advantage of serving as a color indicator, allowing for easy visual confirmation that the composition has been applied to a skin surface. Furthermore, whereas staining of the teats of diary animals has been a concern, it has surprisingly been found that the color of a methylene blue solution is oxidized as it comes into contact with bacterial and, perhaps, as bacteria levels rise when re-application of the composition is needed. Some embodiments of the invention, therefore, provide for a method and composition that reduces or eliminates teat staining and provides, in some cases, an indicator that re-treatment is needed.

In some embodiments, the composition comprises about 0.1 M or more citrate, such as about 0.2 M or more, or about 0.3 M or more citrate. Typically, the composition will comprise no more than about 2 M citrate, such as about 1 M or less, about 0.8 M or less, or about 0.5 M or less. The foregoing amounts also can be expressed as ranges (e.g., about 0.1-2 M, about 0.1-1 M, about 0.1-0.8 M, about 0.2-2 M, about 0.2-1 M, about 0.2-0.8 M, about 0.3-2 M, about 0.3-1 M, about 0.3-0.8 M, about 0.3-0.5 M). Any sub-range thereof also is contemplated.

The citrate can be provided by any suitable source. For instance the citrate can be provided by citric acid, a citrate salt, or a combination thereof. Suitable salts include sodium, potassium, magnesium, or calcium citrate salts. Furthermore, the citrate salt can be a monvalent salt or a multivalent salt, such as a monobasic, dibasic, or tribasic citrate salt (e.g. mono-, di-, or tri-sodium citrate or mono-, di-, or tri-potassium citrate).

In some embodiments, the composition comprises sodium, potassium, magnesium, or calcium ions in a concentration of about 0.1 M or more, such as 0.2 M or more, or even 0.3 M or more. The sodium, potassium, magnesium, or calcium ions can be provided by any suitable source, for instance, by use of sodium, potassium, magnesium, or calcium citrate salts as a source for the citrate.

In some embodiments, the composition comprises about 0.1 mM or more methylene blue, such as about 0.2 mM or more methylene blue, 0.5 mM or more methylene blue, or even 0.8 mM or more methylene blue. Typically, the composition will comprise no more than about 30 mM, or no more than about 10 mM, such as about 3 mM or less, about 2 mM or less, about 1 mM or less, about 0.8 mM or less, about 0.7 mM or less, or about 0.6 mM or less (e.g., about 0.5 mM or less) of methylene blue. The foregoing amounts also can be expressed as ranges (e.g., about 0.1-3 mM, about 0.1-2 mM about 0.1-1 mM, about 0.1-0.8 mM, about 0.1-0.7 mM, about 0.2-1 mM, about 0.2-0.8 mM, about 0.2-0.7 mM). Any sub-range thereof also is contemplated.

In some embodiments, the composition comprises about 10 mM or more alkyl para-hydroxybenzoate, such as about 12 mM or more, or about 15 mM or more. Typically, the composition will comprise no more than about 60 mM or no more than about 50 mM alkyl para-hydroxybenzoate, such as about 40 mM or less, about 30 mM or less, or about 25 mM or less alkyl para-hydroxybenzoate. The foregoing amounts also can be expressed as ranges (e.g., about 10-50, about 10-30 mM, about 10-25 mM, about 12-50 mM, about 12-40 mM, about 12-30 mM, about 12-25 mM, about 15-50 mM, about 15-40 mM, about 15-30 mM, about 15-25 mM). Any sub-range thereof also is contemplated.

Any alkyl para-hydroxybenzoate can be used. Suitable alkyl para-hydroxybenzoates include methyl-, ethyl-, propyl-, and butyl-para-hydroxybenzoate. The composition can comprise more than one type of alkyl para-hydroxybenzoate. For example, the composition can comprise methyl- and ethyl-para-hydroxybenzoate. When more than one type of alkyl para-hydroxybenzoate is used, the combined amount is generally within the ranges discussed above. In one embodiment, the composition comprises about 1-3 mM (e.g., about 1-2 mM) of propyl-parahydroxybenzoate, and the remaining portion of the alkyl para-hydroxybenzoate is methyl-para-hydroxybenzoate. The alkyl para-hydroxybenzoate can be supplied by any source, for instance, a salt of an alkyl para-hydroxybenzoate or an alkyl para-hydroxybenzoic acid.

The composition can further comprise an emollient. Suitable emollients include, for instance, glycerol, propylene glycol, lanolin, glycerin, sorbitol, D-panthenol, poly ethylene glycol (PEG) (e.g., mw. 200-10,000) and esters thereof, acyl lactylates, polyquaternium compounds (polyquaternium-7), glycerol cocoate/laurate, PEG-7 glycerol cocoate, stearic acid, hydrolyzed silk peptide, silk protein, aloe vera gel, guar hydroxypropyltrimonium chloride, alkyl poly glucoside/glyceryl luarate, shea butter and coco butter. In some embodiments, emollients will typically be present in an amount of about 5 wt. % or more, such as about 10 wt. % or more, or even about 15 wt. % or more. In some embodiments, the composition will generally have no more than about 30 wt. % emollients, such as about 25 wt. % or less, or even 20 wt. % or less. In other embodiments (e.g., cold-weather formulations), more emollient may be used, such as about 30 wt. % or more, about 40 wt. % or more, about 50 wt. % or more, or even about 60 wt. % or more or even about 75 wt. % or more.

The composition can further comprise a barrier or film-forming agent, or a thickener. Suitable barrier and film-forming agents and thickeners include, for instance, polyvinylpyrrolidone (PVP), polyvinylalcohol (PVA or PVOH), polyacrylate, polyacrylamide, latex, carbomer, glycerol, hemicelluloses (e.g., arabinoxylanes and glucomannanes); plant gum materials (e.g., guar gum, gum arabic, and johannistree gums); cellulose and derivatives thereof (e.g., methyl cellulose, ethyl cellulose, hydroxypropyl cellulose, hydroxyethyl cellulose, carboxymethyl cellulose, carboxyethyl cellulose; methylhydroxypropylcellulose (HPMC) and ethylhydroxyethylcellulose); starch and starch derivatives (e.g., hydroxyethyl starch or cross linked starch); microbial and sea weed polysaccharides (e.g., xanthan gum, sodium alginate, carrageenan, curdlan, pullulan, and dextran), dextran sulfate, whey, collagen, pectin, gelatin, chitosan, chitosan derivatives, and polysulfonic acids and their salts. Clays and modified clays (e.g., bentonite or laponite), colloidal alumina or silica, and fatty acids or salts thereof can also be used as thickeners, co-thickeners, or stability agents for thickeners. The amount used will depend upon the particular agent selected. Generally, when used, the barrier or film forming agent, or thickener, will be present in an amount of about 0.1 wt. % or more, such as about 1 wt. % or more, 2 wt. % or more, 5 wt. % or more, or even 10 wt. % or more. Typically, the barrier or film forming agent, or thickener, constitute no more than about 40 wt. % of the composition, such as about 35 wt. % or less, 30 wt. % or less, or 25 wt. % or less.

In some embodiments, the composition comprises at least one gelling agent, which can be the same as, or different from, the barrier or film-forming agent or thickener. Gelling agents include any of those agents described as above with respect to the barrier or film-forming agents and thickeners that can produce a gel. By way of non-limiting examples, the gelling agent can be polyvinylpyrrolidone (PVP), polyvinylalcohol (PVA or PVOH), polyacrylate (e.g., cross-linked polyacrylic acid polymers such as the CARBOPOL® products by Lubrizol Corp., or acrylate copolymer Capigel 98™ by Seppic, Inc.), polyacrylamide, latex, carbomer, cellulose or derivative thereof (e.g., methyl cellulose, ethyl cellulose, hydroxypropyl cellulose, hydroxyethyl cellulose, carboxymethyl cellulose, carboxyethyl cellulose; methylhydroxypropylcellulose (HPMC) and ethylhydroxyethylcellulose). The amount used will depend upon the particular agent selected. Generally, when used, the gelling agent will generally be present in an amount of about 0.1 wt % or more, such as about 1 wt. % or more, about 2 wt. % or more, or even about 5 wt. % or more. Typically, the gelling agent will constitute no more than about 50 wt. % or no more than about 40 wt. % of the composition, such as about 35 wt. % or less, or 30 wt. % or less. By way of further illustration, in some applications, the composition will comprise about 1-50 wt. %, or about 1-20 wt. %, such as about 2-10 wt. % or even about 2-5 wt. %, of the gelling agent. In other applications, the composition can comprise about 10-30 wt. % or 20-30 wt. % gelling agent.

The composition can further comprise a surfactant or foaming agent. Surfactants include anionic, cationic, nonionic, zwitterionic and amphoteric surfactants, and can be high foaming, low foaming, moderate foaming, or non foaming type surfactants. Anionic surfactants include, for example, linear alkyl benzene sulfonic acid, linear alkyl benzene sulfonate, alkyl sulfomethyl ester, α-olefin sulfonate, alcohol ether sulfate, alkyl sulfate, alkylsulfo- and dialkylsulfo succinate, and salts thereof. Nonionic surfactants include, for example, alkyl polyglucoside, alkyl ethoxylated alcohol, alkyl propoxylated alcohol, ethoxylatedpropoxylated alcohol, alkylphenol ethoxylates, sorbitan, sorbitan ester, alkanol amide, and polyethoxylated polyoxypropylene block copolymers (poloxamers). Amphoteric surfactants include, for example, alkyl betaines and alkyl amphoacetates (e.g., cocoamidopropyl betaine, sodium cocoamphoacetate, sodium lauroamphoacetate and sodium cocoamphodiacetate).

The principal carrier for the topical composition will typically be water. Generally, the composition will comprise water in an amount of about 15 wt. % or more, about 30 wt. % or more, or about 40 wt. % or more, such as about 60 wt. % or more, or even 70 wt. % or more (e.g., 80 wt. % or more).

The composition also can comprise an alcohol in any suitable amount. Any alcohol can be used, including methanol, ethanol, n-propanol, isopropanol (IPA), and the like. According to some embodiments, the composition comprises lower alcohol concentrations, such as about 0.1 wt. % to about 20 wt. % alcohol, such as about 1 wt. % to about 15 wt. %, or even about 5 wt. % to about 10 wt. % alcohol. Low alcohol levels used in combination with emollients are believed to be especially useful for treating or protecting a mammalian teat in the milking season. A composition that is believed to be particularly advantageous when using a low alcohol content comprises (a) about 0.2-1 M citrate; (b) about 0.01-2 mM or about 0.1-1 mM methylene blue; (c) about 10-50 mM alkyl para-hydroxybenzoate; (d) about 0.1% to about 20% alcohol; and (e) about 5 wt. % or more of an emollient.

According to other embodiments, higher alcohol levels are used, such as about 20 wt. % or more, about 25 wt. % or more, about 30 wt. % or more, about 35 wt. % or more, about 40 wt. % or more, or even about 50 wt. % or more. Typically, no more than about 80% alcohol is used, such as about 70% or less. Such embodiments are thought to be useful when, for instance, a gelling agent is used so as to provide a formulation suitable for use as a teat sealant for dairy mammals in the dry season. A composition believed to be particularly advantageous when using a higher alcohol level comprises (a) about 0.2-1 M citrate; (b) about 0.01-2 mM or about 0.1-1 mM methylene blue; (c) about 10-50 mM alkyl para-hydroxybenzoate; (d) about 20% to about 80% alcohol; and (e) a gelling agent, such as a polyacrylic acid or acrylate copolymer gelling agent.

According to another aspect of the method, the composition can be formulated as a two-part composition. The method comprises applying to the teat a first topical composition comprising a polymer, and a second topical composition comprising a cross-linking agent for the polymer. When both the first and second compositions have been applied to the teat, the polymer and cross-linking agent combine to foam a film or gel, thereby providing a protective coating on the teat. The two-part formulation is believed to be particularly effective as a teat sealant for use on the teats of dairy animals during the dry season.

In the two-part formulation, the first or second compositions, or both, optionally further comprise citrate, methylene blue, or alkyl para-hydroxybenzoate in the amounts previously described. The first or second compositions also can comprise any of the other components described herein. By way of further illustration, the first composition can comprise citrate, methylene blue, and a polymer, and the second composition can comprise citrate, alkyl para-hydroxybenzoate, a cross-linking agent, and, optionally, alcohol. The first and second compositions can be used simultaneously or sequentially in any order. When used sequentially, both compositions should be applied within a time frame that prevents drying of the first-applied composition prior to application of the second-applied composition. In other words, the composition that is applied first should still be wet when the second composition is applied so as to facilitate interaction of the cross-linking agent with the polymer and formation of a gel.

The particular polymer and cross linking agent selected will depend on the intended end-use of the composition and the desired properties of the resulting cross-linked gel. By way of illustration, the polymer can be PVA and the cross-linking agent can be a borate, such as sodium borate (borax). Other suitable polymers and cross-linking agents include polyvinyl acetate, other vinyl monomers and polymers, N-alkyl pyrrolidone, polyester phthalate, polyester sebacat, trioctyl trimellitate and other chemicals known to perform as plasticizers.

One composition that is considered to be particularly effective when used in a two-part formulation comprises (a) citrate; (b) about 0.01-2 mM or about 0.1-1 mM methylene blue; and (c) about 5-50 wt. % water soluble polymer. An effective complimentary composition comprises (a) about 0.2-1 M citrate; (b) about 20-100 mM alkyl para-hydroxybenzoate; (c) about 1-10% alcohol; and (d) a cross-linking agent. Although the compositions are intended to be used together, either simultaneously or sequentially, they should be produced and stored separately (e.g., in separate containers, or in separate chambers of a single container) prior to use. Thus, in addition to the method and individual compositions, a kit is provided herein, which comprises (1) a first composition comprising (a) citrate; (b) about 0.01-2 mM or about 0.1-1 mM methylene blue; and (c) about 5-50 wt. % polymer, such as about 10-40 wt % or 20-30 wt. % polymer (e.g., PVA); and (2) a second composition comprising (a) about 0.2-1 M citrate; (b) about 20-100 mM alkyl para-hydroxybenzoate; (c) about 1-10% alcohol; and (d) a cross-linking agent in an amount sufficient to achieve the desired gel consistency (e.g., borate or sodium borate in any amount, such as about 1-5 wt. %).

The compositions described herein can have any suitable pH. Desirably, the composition will have a pH that will not cause irritation or damage to the skin of a mammal, particularly the skin of a mammalian teat. Thus, the composition will typically have a neutral pH (e.g., about 4-8, about 5-8, or about 6-7). The pH can be adjusted by any suitable method. For instance, the ratio of citrate to citric acid as a source of the citrate ion can be adjusted so as to provide the desired pH. Alternatively, or in addition, a pH adjuster and/or buffer can be used to obtain the desired pH.

The compositions described herein can be formulated as a liquid, foam, or gel, and topically applied in any manner. For instance, the composition can be applied by dipping the teat of a mammal into the composition, or by wiping, brushing, or spraying the composition onto the skin of the teat. The compositions, especially liquid compositions, can have any suitable viscosity. In some instances, however, it may be desired to use a thicker composition so that the composition is retained on the skin of the teat for a longer period of time without dripping. Thus, the composition can be formulated so as to have a higher viscosity, such as about 50 cP or more, about 100 cp or more, about 200 cp or more, about 500 cP or more, about 1000 cP or more, about 2500 cp or more, or even about 5000 cp or more. The viscosity of the composition will typically be less than about 10,000 cp. Viscosity refers to the kinematic viscosity measured at standard temperature and pressure (25° C. and 1 atm).

In preferred embodiments, the compositions described herein provide an antimicrobial effect when applied to the skin of a mammal, especially the skin of the teat of a dairy animal. As previously mentioned, it is believed that this effect is primarily the result of the combined action of the citrate, methylene blue, and alkyl para-hydroxybenzoate, and perhaps alcohol. The composition can further comprise additional antibiotic or antimicrobial agents, particularly topical antibiotic or antimicrobial agents, such as such as iodine-containing antiseptics (e.g., iodine or iodophors); chlorine based antiseptics (e.g., hypochlorites (e.g., sodium hypochlorite; anolyte); antiseptic plant oils; phenols; quaternary ammonium compounds; antiseptic surfactants; bisbiguanides (e.g., chorhexidine); terpenes; sodium bicarbonate; sulfates; guanidine salts; formaldehyde-releasing compounds; ascorbic acid; and peracids/peroxides.

While the compositions described herein can be formulated with additional antibiotic or antiseptic components, one of the advantages of at least some compositions described herein is that such additional antibiotic or antiseptic agents are not required. Thus, in additional embodiments, the compositions described herein can be substantially free (e.g., contains less than an antimicrobial-effective amount) or completely free of one or more common topical antibiotic or antiseptic agents, such as those mentioned above. Alternatively, the compositions can be substantially free or completely free of any antiseptic or antimicrobial agent other than citrate, methylene blue, alkyl para-hydroxybenzoate, and alcohol.

The compositions described herein can be provided in any suitable container. In one embodiment, the container is an applicator suitable for applying the composition to the skin of the teat of a dairy animal. Such an applicator can comprise, for instance, a cup portion of a size and shape that will allow the teat to be inserted into the cup and contact the topical composition. When two-part compositions are used, the applicator can optionally comprise two cup portions: a first cup portion containing a first composition, and a second cup portion containing a second composition. Alternatively, a single cup portion with two separate reservoirs might be used, wherein each reservoir contains one of the two topical compositions and each reservoir is fluidly connected to the cup portion such that the compositions can be delivered to the cup portion simultaneously or sequentially.

The methods and compositions described herein are useful with respect to any type of mammal, particularly a food-producing mammal such as a dairy animal. The methods and compositions described herein may be particularly useful for treating or protecting the teats of food-producing mammals susceptible to teat infections, such as mastitis, and, thus, may be particularly useful in treating or protecting the teats of dairy cows.

Any composition as described above can be used in the method of treating or protecting a mammalian teat, without limitation. Furthermore, each of the foregoing compositions described in the context of the method of treating or protecting a mammalian teat is considered to be a separate aspect of the invention. Although these compositions have been described in the context of a method of treating or protecting a mammalian teat, they are not limited to any particular intended use, and have other practical applications, both in the agricultural and dairy industries, and in other contexts. For instance, they can be used as general antimicrobial compositions, skin and would cleansing compositions, protective barrier film-forming compositions, and moisturizing compositions, especially for the skin of humans and animals.

The following examples further illustrate the invention but, of course, should not be construed as in any way limiting its scope.

EXAMPLE 1

This example demonstrates the antimicrobial properties of compositions of the invention.

Eight compositions (compositions 1-8) were prepared using the components identified in Table 1. Each composition was tested in vitro at six different concentrations to determine the antimicrobial effect against four strains of bacteria: methicillin-sensitive *Staphylococcus aureus* (MSSA), methicillin-resistant *Staphylococcus aureus* (MRSA), and two strains of *E. coli*. Tests were run in duplicate, and performed in accordance with the procedures set forth in Clinical and Laboratory Standards Institute (CLSI) reference M-100. The results are provided in Tables 2-9, wherein the minimum inhibitory concentration (MIC) is the concentration required to inhibit visible growth of the microorganism, and the minimum bactericidal concentration (MBC) is the concentration required to kill the microorganism. The results show that the tested compositions had a substantial antimicrobial effect.

TABLE 1

| Component | Composition No. | | | | | | | |
|---|---|---|---|---|---|---|---|---|
| | 1 | 2 | 3 | 4 | 5 | 6 | 7 | 8 |
| Trisodium Citrate Dihydrate, Granular, USP | 10% | 10% | 10% | 20% | 10% | 20% | 10% | 20% |
| Citric Acid Anhydrous, Powder USP | 0.11% | 0.15% | 0.14% | 0.24% | 0.14% | 0.17% | 0.13% | 0.26% |
| Methylene Blue Trihydrate USP | 0.02% | 0.01% | 0.01% | 0.01% | 0.02% | 0.01% | 0.02% | 0.01% |
| Methylparaben NF | 0.2% | 0.3% | 0.2% | 0.2% | 0.2% | 0.2% | 0.2% | 0.2% |
| Propylparaben NF | 0.02% | 0.03% | 0.02% | 0.02% | 0.02% | 0.02% | 0.02% | 0.02% |
| Isopropyl Alcohol | 5% | 5% | 10% | 5% | — | — | 5% | 5% |
| Xanthan Gum | — | — | — | — | — | — | — | 0.45% |
| PVP K60 Solution | — | — | — | — | — | — | 1% | — |
| Glycerol | 3% | 3% | 3% | 3% | 3% | 3% | 10% | 8% |
| Propylene Glycol | 2% | 2% | 2% | 2% | 2% | 2% | 3.8% | 2% |
| Water | 79.65% | 79.51% | 74.63% | 69.53% | 84.62% | 74.60% | 69.83% | 64.07% |
| pH | 6.5-7 | 6.4-6.8 | 6.5-6.9 | 6.5-6.8 | 6.4-6.7 | 6.5-6.9 | 6.5-6.8 | 6.5-6.7 |

*All amounts are expressed as weight percentages.

TABLE 2

| | Dilution (ug/ul) of Composition 1 | | | | | | | | | |
|---|---|---|---|---|---|---|---|---|---|---|
| # | 1/4 1 | 1/8 2 | 1/16 3 | 1/32 4 | 1/64 5 | 1/128 6 | Control 12 | Organism | MIC | MBC |
| A | | | | * | * | * | * | MSSA | 1/32 | 1/8 |
| B | | | | * | * | * | * | MSSA | | |
| C | | | | * | * | * | * | MRSA | 1/32 | 1/8 |

TABLE 2-continued

Dilution (ug/ul) of Composition 1

| # | ¼ 1 | ⅛ 2 | 1/16 3 | 1/32 4 | 1/64 5 | 1/128 6 | Control 12 | Organism | MIC | MBC |
|---|---|---|---|---|---|---|---|---|---|---|
| D |  |  |  | * | * | * | * | MRSA |  |  |
| E | ** | * | * | * | * | * | * | EC | ⅛ | ⅛ |
| F | ** | * | * | * | * | * | * | EC |  |  |
| G | ** | * | * | * | * | * | * | EC (strain 2) | ⅛ | ⅛ |
| H | ** | * | * | * | * | * | * | EC (strain 2) |  |  |

TABLE 3

Dilution (ug/ul) of Composition 2

| # | ¼ 1 | ⅛ 2 | 1/16 3 | 1/32 4 | 1/64 5 | 1/128 6 | Control 12 | Organism | MIC | MBC |
|---|---|---|---|---|---|---|---|---|---|---|
| A | * | * | * | * | * | * | * | MSSA | ⅛ | <¼ |
| B | * | * | * | * | * | * | * | MSSA |  |  |
| C | * | * | * | * | * | * | * | MRSA | ⅛ | <¼ |
| D | * | * | * | * | * | * | * | MRSA |  |  |
| E | * | * | * | * | * | * | * | EC | ⅛ | <¼ |
| F | * | * | * | * | * | * | * | EC |  |  |
| G | * | * | * | * | * | * | * | EC (strain 2) | ⅛ | <¼ |
| H | * | * | * | * | * | * | * | EC (strain 2) |  |  |

TABLE 4

Dilution (ug/ul) of Composition 3

| # | ¼ 1 | ⅛ 2 | 1/16 3 | 1/32 4 | 1/64 5 | 1/128 6 | Control 12 | Organism | MIC | MBC |
|---|---|---|---|---|---|---|---|---|---|---|
| A |  | * | * | * | * | * | * | MSSA | 1/16 | ⅛ |
| B |  | * | * | * | * | * | * | MSSA |  |  |
| C |  | * | * | * | * | * | * | MRSA | 1/16 | <¼ |
| D |  | * | * | * | * | * | * | MRSA |  |  |
| E | * | * | * | * | * | * | * | EC | ⅛ | <¼ |
| F | * | * | * | * | * | * | * | EC |  |  |
| G | * | * | * | * | * | * | * | EC (strain 2) | ⅛ | <¼ |
| H | * | * | * | * | * | * | * | EC (strain 2) |  |  |

TABLE 5

Dilution (ug/ul) of Composition 4

| # | ¼ 1 | ⅛ 2 | 1/16 3 | 1/32 4 | 1/64 5 | 1/128 6 | Control 12 | Organism | MIC | MBC |
|---|---|---|---|---|---|---|---|---|---|---|
| A |  |  |  | * | * | * | * | MSSA | 1/64 | 1/16 |
| B |  |  |  | * | * | * | * | MSSA |  |  |
| C |  |  |  | * | * | * | * | MRSA | 1/64 | 1/16 |
| D |  |  |  | * | * | * | * | MRSA |  |  |
| E | * | * | * | * | * | * | * | EC | ⅛ | <¼ |
| F | * | * | * | * | * | * | * | EC |  |  |
| G | * | * | * | * | * | * | * | EC (strain 2) | ⅛ | <¼ |
| H | * | * | * | * | * | * | * | EC (strain 2) |  |  |

TABLE 6

Dilution (ug/ul) of Composition 5

| # | ¼ 1 | ⅛ 2 | 1/16 3 | 1/32 4 | 1/64 5 | 1/128 6 | Control 12 | Organism | MIC | MBC |
|---|---|---|---|---|---|---|---|---|---|---|
| A |  | ** | * | * | * | * | * | MSSA | 1/16 | 1/16 |
| B |  | ** | * | * | * | * | * | MSSA |  |  |
| C |  | ** | * | * | * | * | * | MRSA | 1/16 | 1/16 |
| D |  | ** | * | * | * | * | * | MRSA |  |  |
| E | * | * | * | * | * | * | * | EC | ⅛ | ¼ |
| F | * | * | * | * | * | * | * | EC |  |  |
| G | * | * | * | * | * | * | * | EC (strain 2) | ⅛ | ¼ |
| H | * | * | * | * | * | * | * | EC (strain 2) |  |  |

TABLE 7

Dilution (ug/ul) of Composition 6

| # | ¼ 1 | ⅛ 2 | 1/16 3 | 1/32 4 | 1/64 5 | 1/128 6 | Control 12 | Organism | MIC | MBC |
|---|---|---|---|---|---|---|---|---|---|---|
| A |  |  |  | * | * | * | * | MSSA | 1/32 | 1/16 |
| B |  |  |  | * | * | * | * | MSSA |  |  |
| C |  |  |  | * | * | * | * | MRSA | 1/32 | 1/16 |
| D |  |  |  | * | * | * | * | MRSA |  |  |
| E | ** | * | * | * | * | * | * | EC | ⅛ | <¼ |
| F | ** | * | * | * | * | * | * | EC |  |  |
| G | ** | * | * | * | * | * | * | EC (strain 2) | ⅛ | <¼ |
| H | ** | * | * | * | * | * | * | EC (strain 2) |  |  |

TABLE 8

Dilution (ug/ul) of Composition 7

| # | ¼ 1 | ⅛ 2 | 1/16 3 | 1/32 4 | 1/64 5 | 1/128 6 | Control 12 | Organism | MIC | MBC |
|---|---|---|---|---|---|---|---|---|---|---|
| A |  |  |  |  |  | * | * | MSSA | 1/128 | 1/32 |
| B |  |  |  |  |  | * | * | MSSA |  |  |
| C |  |  |  |  |  | * | * | MRSA | 1/128 | 1/32 |
| D |  |  |  |  |  | * | * | MRSA |  |  |
| E |  | * | * | * | * | * | * | EC | ⅛ | <¼ |
| F |  | * | * | * | * | * | * | EC |  |  |
| G |  | * | * | * | * | * | * | EC (strain 2) | ⅛ | <¼ |

TABLE 8-continued

Dilution (ug/ul) of Composition 7

| # | ¼ 1 | ⅛ 2 | 1/16 3 | 1/32 4 | 1/64 5 | 1/128 6 | Control 12 | Organism | MIC | MBC |
|---|---|---|---|---|---|---|---|---|---|---|
| H |  |  | * | * | * | * | * | EC (strain 2) |  |  |

TABLE 9

Dilution (ug/ul) of Composition 8

| # | ¼ 1 | ⅛ 2 | 1/16 3 | 1/32 4 | 1/64 5 | 1/128 6 | Control 12 | Organism | MIC | MBC |
|---|---|---|---|---|---|---|---|---|---|---|
| A |  |  | * | * | * | * | * | MSSA | 1/32 | ⅛ |
| B |  |  | * | * | * | * | * | MSSA |  |  |
| C |  |  | * | * | * | * | * | MRSA | 1/32 | ⅛ |
| D |  |  | * | * | * | * | * | MRSA |  |  |
| E |  | * | * | * | * | * | * | EC | 1/16 | <¼ |
| F |  | * | * | * | * | * | * | EC |  |  |
| G |  | * | * | * | * | * | * | EC (strain 2) | 1/16 | <¼ |
| H |  |  | * | * | * | * | * | EC (strain 2) |  |  |

EXAMPLE 2

The compositions provided in Table 10 further illustrate the compositions of the invention. The "Part A" and "Part B" compositions are intended for use together, simultaneously or sequentially in any order. The "Hydrogel" compositions illustrate single-part compositions that comprise a gelling agent.

TABLE 10

| Ingredient | PVA Part A | PVA Part B | Hydrogel-1 | Hydrogel-2 |
|---|---|---|---|---|
| Trisodium Citrate Dihydrate, Granular, USP | 1% | 10% | 0.4% | 5% |
| Citric Acid Anhydrous, Powder USP | 0.25% | 0.25% | 4% | 2.5% |
| Methylene Blue Trihydrate USP | 0.03% | — | 0.015% | 0.01% |
| Methylparaben NF | — | 0.70% | 0.35% | 0.20% |
| Propylparaben NF | — | 0.07% | 0.035% | 0.02% |
| Isopropyl Alcohol | — | 5% | 45% | 45% |
| PVA (Elvanol 51-05) | 25% | — | — | — |
| Borax | — | 3% | — | — |
| HPMC (Methocel 40-100 PCG) | — | — | 4% | — |
| Carbopol 674 | — | — | 0.18% | — |
| Capigel 98 | — | — | — | 2% |
| Water | 73.72% | 80.98% | 46.02% | 45.27% |

*All amounts are expressed as weight percentages.

EXAMPLE 3

The following example illustrates additional compositions that can be prepared in accordance with the invention, as set forth in Tables 11-13.

TABLE 11

| Component | Amount |
|---|---|
| Citrate salt (e.g., trisodium Citrate Dihydrate) | about 1-50%, about 5-50%, about 5-30% or about 10-20% |
| Citric Acid | about 0.05-1%, about 0.05-0.5%, or about 0.1-0.3% |
| Methylene Blue (e.g., Methylene Blue Trihydrate) | about 0.005-1%, about 0.005-0.05%, about 0.01-0.05%, or about 0.01-0.02% |
| Methyl-paraben | about 0.1-1%, about 0.1-0.6%, about 0.1-0.5%, or about 0.2-0.3% |
| Propyl-paraben | about 0.01-1%, about 0.1-0.06%, about 0.01-0.05%, or about 0.02-0.03% |
| Alcohol (e.g., Isopropyl Alcohol) | about 0-20%, about 5-15%, or about 5-10% |
| optional film former or thickener (e.g., Xanthan Gum) | about 0.2-1%, or about 0.3-0.5% |
| optional film former or thickener (e.g., PVP K60) | about 0.5-10%, or about 1-5% |
| optional emollient (e.g., Glycerol) | about 1-15%, or about 3-10% |
| optional emollient (e.g., Propylene Glycol) | about 1-5%, or about 2-4% |
| optional surfactants and/or foaming agents | about 0.1-2%, or about 0.1-1% |
| Water | remainder, or about 60-80% |
| pH | about 4-8, or about 6-7 |

*All amounts expressed as weight percentages.

TABLE 12

| Component | Two Part Formulation | |
| --- | --- | --- |
| | Part A | Part B |
| Citrate salt (e.g., trisodium Citrate Dihydrate) | about 0-5% | about 5-10% |
| Citric Acid | about 0-1% | about 0-1% |
| Methylene Blue (e.g., Methylene Blue Trihydrate) | about 0.01-0.1%, or about 0.01-0.05% | — |
| Methyl-paraben | — | about 0.1-1%, or about 0.05%-1% |
| Propyl-paraben | — | about 0.01%-0.1%, or about 0.05%-0.1% |
| Alcohol (e.g., Isopropyl Alcohol) | — | about 1-10%, or about 2-8% |
| Polymer (e.g., PVA) | about 10-40%, or about 20-30% | — |
| Cross-linking agent (e.g., Borax) | — | about 1-5% |
| Water | remainder, or about 60-80% | remainder, or about 70-90% |

*All amounts are expressed as weight percentages.

TABLE 13

| Ingredient | Hydrogel-1 | Hydrogel-2 |
| --- | --- | --- |
| Citrate salt (e.g., trisodium Citrate Dihydrate) | about 0.1-1%, or about 0.1-0.5% | about 1-10%, or about 2-8% |
| Citric Acid | about 1-10%, or about 2-8% | about 1-5%, or about 2-4% |
| Methylene Blue (e.g., Methylene Blue Trihydrate) | about 0.005-0.02% | about 0.005-0.02% |
| Methyl-paraben | about 0.1-0.5% | about 0.1-0.5% |
| Propyl-paraben | about 0.01-0.05% | about 0.01-0.05% |
| Alcohol (e.g., Isopropyl Alcohol) | about 30-60%, or about 40-50% | about 30-60%, or about 40-50% |
| Gelling agent (e.g., HPMC) | about 1-10%, or about 2-5% | — |
| Gelling agent/thickener (e.g., polyacrylic acid, such as Carbopol 674) | about 0.1-1%, or about 0.1-0.5% | — |
| Gelling agent/thickener (e.g., acrylates copolymer, such as Capigel 98) | — | about 1-5% |
| Water | remainder, or about 40-60% | remainder, or about 40-60% |

*All amounts are expressed as weight percentages.

EXAMPLE 4

The following example demonstrates the antimicrobial properties of compositions prepared accordance with the invention.

An in vitro time-kill study was used to evaluate the antimicrobial properties of a test composition and a positive control product, with and without organic soil loads (FBS Dilution), when challenged with five American Type Culture Collection (ATCC) microorganism strains. The percent and log 10 reductions from the initial population of each challenge species were determined following 30-second, 2-minute, and 5-minute exposures to the test and positive control compositions. All agar-plating was performed in duplicate. The test composition contained Trisodium Citrate 10%; Parabens 0.3%; and Methylene Blue 0.05%. The positive control contained 5000 ppm iodine as an active ingredient. The results are presented in Tables 14-23, below.

As the results show, the test composition exhibited excellent antimicrobial properties, which was at least as effective as the positive control composition at most FBS dilutions against the tested strains.

TABLE 14

| | Test composition: No FBS Dilution | | | | |
| --- | --- | --- | --- | --- | --- |
| Microorganism Species (ATCC #) | Initial Population (CFU/mL) | Exposure Time | Post-Exposure Population (CFU/mL) | $Log_{10}$ Reduction | Percent Reduction |
| Corynebacterium bovis (ATCC #7715) | $1.910 \times 10^8$ | 30 seconds | $7.050 \times 10^6$ | 1.4328 | 96.3089% |
| | | 2 minutes | $4.40 \times 10^6$ | 1.6375 | 97.6963% |
| | | 5 minutes | $6.20 \times 10^6$ | 1.4886 | 96.7539% |
| Escherichia coli (ATCC #11229) | $1.2150 \times 10^9$ | 30 seconds | $<1.00 \times 10^3$ | 6.0846 | 99.9999% |
| | | 2 minutes | $<1.00 \times 10^3$ | 6.0846 | 99.9999% |
| | | 5 minutes | $<1.00 \times 10^3$ | 6.0846 | 99.9999% |
| Pseudomonas aeruginosa (ATCC #15442) | $1.1150 \times 10^9$ | 30 seconds | $1.0150 \times 10^6$ | 3.0408 | 99.9090% |
| | | 2 minutes | $<1.00 \times 10^3$ | 6.0473 | 99.9999% |
| | | 5 minutes | $<1.00 \times 10^3$ | 6.0473 | 99.9999% |
| Staphylococcus aureus aureus (ATCC #6538) | $8.750 \times 10^8$ | 30 seconds | $4.40 \times 10^5$ | 3.2985 | 99.9497% |
| | | 2 minutes | $<1.00 \times 10^3$ | 5.9420 | 99.9999% |
| | | 5 minutes | $<1.00 \times 10^3$ | 5.9420 | 99.9999% |
| Streptococcus agalactiae (ATCC #12386) | $1.1750 \times 10^{10}$ | 30 seconds | $<1.00 \times 10^3$ | 7.0700 | 99.9999% |
| | | 2 minutes | $<1.00 \times 10^3$ | 7.0700 | 99.9999% |
| | | 5 minutes | $<1.00 \times 10^3$ | 7.0700 | 99.9999% |

TABLE 15

| | | | | | |
|---|---|---|---|---|---|
| Positive Control (Iodine): No FBS Dilution | | | | | |
| Microorganism Species (ATCC #) | Initial Population (CFU/mL) | Exposure Time | Post-Exposure Population (CFU/mL) | $Log_{10}$ Reduction | Percent Reduction |
| *Corynebacterium bovis* (ATCC #7715) | $1.910 \times 10^8$ | 30 seconds | $3.550 \times 10^6$ | 1.7308 | 98.1414% |
| | | 2 minutes | $3.90 \times 10^6$ | 1.6899 | 97.9581% |
| | | 5 minutes | $2.440 \times 10^6$ | 1.8936 | 98.7225% |
| *Escherichia coli* (ATCC #11229) | $1.2150 \times 10^9$ | 30 seconds | $<1.00 \times 10^3$ | 6.0846 | 99.9999% |
| | | 2 minutes | $<1.00 \times 10^3$ | 6.0846 | 99.9999% |
| | | 5 minutes | $<1.00 \times 10^3$ | 6.0846 | 99.9999% |
| *Pseudomonas aeruginosa* (ATCC #15442) | $1.1150 \times 10^9$ | 30 seconds | $1.00 \times 10^3$ | 6.0473 | 99.9999% |
| | | 2 minutes | $<1.00 \times 10^3$ | 6.0473 | 99.9999% |
| | | 5 minutes | $<1.00 \times 10^3$ | 6.0473 | 99.9999% |
| *Staphylococcus aureus aureus* (ATCC #6538) | $8.750 \times 10^8$ | 30 seconds | $<1.00 \times 10^3$ | 5.9420 | 99.9999% |
| | | 2 minutes | $<1.00 \times 10^3$ | 5.9420 | 99.9999% |
| | | 5 minutes | $<1.00 \times 10^3$ | 5.9420 | 99.9999% |
| *Streptococcus agalactiae* (ATCC #12386) | $1.1750 \times 10^{10}$ | 30 seconds | $5.00 \times 10^3$ | 6.3710 | 99.9999% |
| | | 2 minutes | $<1.00 \times 10^3$ | 7.0700 | 99.9999% |
| | | 5 minutes | $<1.00 \times 10^3$ | 7.0700 | 99.9999% |

TABLE 16

| | | | | | |
|---|---|---|---|---|---|
| Test Composition: 5% Fetal Bovine Serum | | | | | |
| Microorganism Species (ATCC #) | Initial Population (CFU/mL) | Exposure Time | Post-Exposure Population (CFU/mL) | $Log_{10}$ Reduction | Percent Reduction |
| *Escherichia coli* (ATCC #11229) | $1.2150 \times 10^9$ | 30 seconds | $<1.00 \times 10^3$ | 6.0846 | 99.9999% |
| | | 2 minutes | $<1.00 \times 10^3$ | 6.0846 | 99.9999% |
| | | 5 minutes | $<1.00 \times 10^3$ | 6.0846 | 99.9999% |
| *Staphylococcus aureus aureus* (ATCC #6538) | $8.750 \times 10^8$ | 30 seconds | $4.40 \times 10^6$ | 2.2985 | 99.4971% |
| | | 2 minutes | $<1.00 \times 10^3$ | 5.9420 | 99.9999% |
| | | 5 minutes | $<1.00 \times 10^3$ | 5.9420 | 99.9999% |

TABLE 17

| | | | | | |
|---|---|---|---|---|---|
| Positive Control: 5% Fetal Bovine Serum | | | | | |
| Microorganism Species (ATCC #) | Initial Population (CFU/mL) | Exposure Time | Post-Exposure Population (CFU/mL) | $Log_{10}$ Reduction | Percent Reduction |
| *Escherichia coli* (ATCC #11229) | $1.2150 \times 10^9$ | 30 seconds | $<1.00 \times 10^3$ | 6.0846 | 99.9999% |
| | | 2 minutes | $<1.00 \times 10^3$ | 6.0846 | 99.9999% |
| | | 5 minutes | $<1.00 \times 10^3$ | 6.0846 | 99.9999% |
| *Staphylococcus aureus aureus* (ATCC #6538) | $8.750 \times 10^8$ | 30 seconds | $<1.00 \times 10^3$ | 5.9420 | 99.9999% |
| | | 2 minutes | $<1.00 \times 10^3$ | 5.9420 | 99.9999% |
| | | 5 minutes | $<1.00 \times 10^3$ | 5.9420 | 99.9999% |

TABLE 18

| | | | | | |
|---|---|---|---|---|---|
| Test Compositoin: 10% Fetal Bovine Serum | | | | | |
| Microorganism Species (ATCC #) | Initial Population (CFU/mL) | Exposure Time | Post-Exposure Population (CFU/mL) | $Log_{10}$ Reduction | Percent Reduction |
| *Escherichia coli* (ATCC #11229) | $1.2150 \times 10^9$ | 30 seconds | $2.050 \times 10^4$ | 4.7728 | 99.9983% |
| | | 2 minutes | $<1.00 \times 10^3$ | 6.0846 | 99.9999% |
| | | 5 minutes | $<1.00 \times 10^3$ | 6.0846 | 99.9999% |
| *Staphylococcus aureus aureus* (ATCC #6538) | $8.750 \times 10^8$ | 30 seconds | $2.270 \times 10^7$ | 1.5860 | 97.4057% |
| | | 2 minutes | $7.50 \times 10^3$ | 5.0669 | 99.9991% |
| | | 5 minutes | $<1.00 \times 10^3$ | 5.9420 | 99.9999% |

TABLE 19

Positive Control: 10% Fetal Bovine Serum

| Microorganism Species (ATCC #) | Initial Population (CFU/mL) | Exposure Time | Post-Exposure Population (CFU/mL) | $Log_{10}$ Reduction | Percent Reduction |
|---|---|---|---|---|---|
| Escherichia coli (ATCC #11229) | $1.2150 \times 10^9$ | 30 seconds | $<1.00 \times 10^3$ | 6.0846 | 99.9999% |
|  |  | 2 minutes | $<1.00 \times 10^3$ | 6.0846 | 99.9999% |
|  |  | 5 minutes | $<1.00 \times 10^3$ | 6.0846 | 99.9999% |
| Staphylococcus aureus aureus (ATCC #6538) | $8.750 \times 10^8$ | 30 seconds | $9.90 \times 10^5$ | 2.9464 | 99.8869% |
|  |  | 2 minutes | $<1.00 \times 10^3$ | 5.9420 | 99.9999% |
|  |  | 5 minutes | $<1.00 \times 10^3$ | 5.9420 | 99.9999% |

TABLE 20

Test Composition: 20% Fetal Bovine Serum

| Microorganism Species (ATCC #) | Initial Population (CFU/mL) | Exposure Time | Post-Exposure Population (CFU/mL) | $Log_{10}$ Reduction | Percent Reduction |
|---|---|---|---|---|---|
| Escherichia coli (ATCC #11229) | $1.2150 \times 10^9$ | 30 seconds | $1.70 \times 10^4$ | 4.8542 | 99.9986% |
|  |  | 2 minutes | $<1.00 \times 10^3$ | 6.0846 | 99.9999% |
|  |  | 5 minutes | $<1.00 \times 10^3$ | 6.0846 | 99.9999% |
| Staphylococcus aureus aureus (ATCC #6538) | $8.750 \times 10^8$ | 30 seconds | $2.2250 \times 10^8$ | 0.5947 | 74.5714% |
|  |  | 2 minutes | $1.630 \times 10^6$ | 2.7298 | 99.8137% |
|  |  | 5 minutes | $1.450 \times 10^4$ | 4.7806 | 99.9983% |

TABLE 21

Positive Control: 20% Fetal Bovine Serum

| Microorganism Species (ATCC #) | Initial Population (CFU/mL) | Exposure Time | Post-Exposure Population (CFU/mL) | $Log_{10}$ Reduction | Percent Reduction |
|---|---|---|---|---|---|
| Escherichia coli (ATCC #11229) | $1.2150 \times 10^9$ | 30 seconds | $2.550 \times 10^5$ | 3.6781 | 99.9790% |
|  |  | 2 minutes | $<1.00 \times 10^3$ | 6.0846 | 99.9999% |
|  |  | 5 minutes | $<1.00 \times 10^3$ | 6.0846 | 99.9999% |
| Staphylococcus aureus aureus (ATCC #6538) | $8.750 \times 10^8$ | 30 seconds | $2.240 \times 10^7$ | 1.5918 | 97.4400% |
|  |  | 2 minutes | $<1.00 \times 10^3$ | 5.9420 | 99.9999% |
|  |  | 5 minutes | $<1.00 \times 10^3$ | 5.9420 | 99.9999% |

TABLE 22

Test Composition: 50% Fetal Bovine Serum

| Microorganism Species (ATCC #) | Initial Population (CFU/mL) | Exposure Time | Post-Exposure Population (CFU/mL) | $Log_{10}$ Reduction | Percent Reduction |
|---|---|---|---|---|---|
| Escherichia coli (ATCC #11229) | $1.2150 \times 10^9$ | 30 seconds | $1.7850 \times 10^6$ | 2.8330 | 99.8531% |
|  |  | 2 minutes | $2.00 \times 10^3$ | 5.7836 | 99.9998% |
|  |  | 5 minutes | $<1.00 \times 10^3$ | 6.0846 | 99.9999% |
| Staphylococcus aureus aureus (ATCC #6538) | $8.750 \times 10^8$ | 30 seconds | $1.0350 \times 10^9$ | 0.0000 | 0.0000% |
|  |  | 2 minutes | $9.750 \times 10^8$ | 0.0000 | 0.0000% |
|  |  | 5 minutes | $4.40 \times 10^8$ | 0.2985 | 49.7143% |

TABLE 23

| | | Positive Control: 50% Fetal Bovine Serum | | | |
|---|---|---|---|---|---|
| Microorganism Species (ATCC #) | Initial Population (CFU/mL) | Exposure Time | Post-Exposure Population (CFU/mL) | $\text{Log}_{10}$ Reduction | Percent Reduction |
| Escherichia coli (ATCC #11229) | $1.2150 \times 10^9$ | 30 seconds | $4.90 \times 10^6$ | 2.3944 | 99.5967% |
| | | 2 minutes | $<1.00 \times 10^3$ | 6.0846 | 99.9999% |
| | | 5 minutes | $<1.00 \times 10^3$ | 6.0846 | 99.9999% |
| Staphylococcus aureus aureus (ATCC #6538) | $8.750 \times 10^8$ | 30 seconds | $4.050 \times 10^8$ | 0.3345 | 53.7143% |
| | | 2 minutes | $5.30 \times 10^7$ | 1.2177 | 93.9429% |
| | | 5 minutes | $1.090 \times 10^5$ | 3.9046 | 99.9875% |

EXAMPLE 5

The following example illustrates a test for the effectiveness of a composition prepared in accordance with the invention when used as post-milking teat conditioner.

Test and positive control teat conditioning compositions are applied to the teats of 24 early-mid lactation Jersey cows post-milking. The test compositions contain about 10-20 wt. % trisodium citrate, about 0.2 wt. % citric acid, about 0.2-0.3 wt. % paraben, and various concentrations of methylene blue (MB) (about 0.01 wt. %, 0.02 wt. %, and 0.04 wt. %) and emollient (about 5, 10, and 11 wt. %). The test compositions have formulations similar to the compositions described in Example 1, as indicated in Table 24. A positive control composition contains 1 wt. % iodine and 12 wt. % emollient.

The 24 early-mid lactation Jersey cows are tested in a single pen, with 12 cows having a blue leg band (BLB group) applied to designate them as one trial group and the other 12 having no leg band (NLB group). Left teats (controls) of all 24 cows are post dipped with the control composition, while right side teats are dipped with a test composition. Both treatment groups are initially dipped with test compositions comprising 0.01% methylene blue dip (day 0), but having different emollient compositions (5 wt. % v 11 wt. %). Thereafter, the test compositions are changed to a 0.02 wt. % MB formulation (day 12) to enhance teat skin coloration. Teats of the NLB group are switched to a 0.04 wt. % MB dip with 11% emollients (day 21) to potentially further enhance coloration. Teats in the BLB group are switched to a higher emollient (10 wt. v 5 wt. %) no drip teat dip (day 23) for the last week of the trial. A summary of the emollient and MB concentrations is provided in Table 24. The trial is 4.5 weeks in duration. All other farm and milking practices are similar across all 4.5 weeks.

TABLE 24

| Blue Leg bands (BLB) | | | | No Leg Bands (NLB) | | | |
|---|---|---|---|---|---|---|---|
| Day | Comp. from Ex. 1 | Emollient (wt. %) | MB (wt. %) | Day | Comp. from Ex. 1 | Emollient (wt. %) | MB (wt. %) |
| 0 | 4 | 5 | 0.01 | 0 | 7 (w/decreased MB) | 11 | 0.01 |
| 12 | 4 (w/increased MB) | 5 | 0.02 | 12 | 7 | 11 | 0.02 |
| 23 | 8 | 10 | 0.01 | 21 | 7 (w/increased MB) | 11 | 0.04 |

Cows are milked twice a day in a double 12 parallel parlor. Cows are forestripped (3 strips/teat) and pre-dipped (6 cow sequence), then dried with terry cloth towels prior to milker unit attachment. Automatic detachers are set at 1.8 lb. flow rate and 1 second delay. All cows are housed in a single pen in a free stall barn with mattresses and sawdust shavings bedding.

Data collection is initiated on Day 1 and continued until Day 30. Test products are applied at Day 0 at the pm milking with subsequent first data observations the following am milking on Day 1. Teat coloration (blue coloration due to MB) is evaluated before teat sanitation/preparation at the subsequent milking after dipping (BP), after premilking teat sanitation (AP), and after milker unit removal (postmilking—AM) using a 0-2 scale (0=no color; 1=light blue; 2=dark blue). Teat skin and teat end scoring is performed using a variation of the Goldberg and Timms methods, respectively, by trained graders (Tables 25 and 26). Scoring is performed at both milkings for the first 4 trial days, then three times per week. Data is entered into an Excel database. Results are compiled and analyzed using SAS.

TABLE 25

| Skin Score | Description |
|---|---|
| 0 | Teat skin has been subjected to physical injury (stepped on/frost bit) |
| 1 | Teat skin is smooth, soft and free of any scales, cracks, or chapping. |

TABLE 25-continued

| Skin Score | Description |
|---|---|
| 2 | Teat skin shows some evidence of scaling especially when feeling (areas of dryness by feeling drag when sliding a gloved hand along the teat barrel &/or seeing areas of lower reflective sheen to the surface of the skin). |
| 3 | Teat skin is chapped. Chapping is where visible bits of skin are visibly peeling. |
| 4 | Teat skin is chapped and cracked. Redness, indicating inflammation, is evident. |
| 5 | Teat skin is severely damaged/ulcerated/open lesions. |

TABLE 26

| Teat End Scoring system | Degree of hyperkeratosis or callousing | | | | |
|---|---|---|---|---|---|
| Cracking | none | minor | mild | moderate | severe |
| A. No cracking or roughness | 1 | 1.5 | 2 | 2.5 | 3 |
| B. Cracked and/or rough | — | 3.5 | 4 | 4.5 | 5 |

*Zero score indicates physical injury of teat.

Mixed procedure of SAS with repeated measured (mixed model with quarter within cow as a repeated measure) is used to analyze teat skin and teat end data, with p<0.05 considered significant. GENMOD procedures of SAS with repeated measures (generalized linear model with quarter within cow as repeated measure) is used to analyzed % cracked/rough teat ends and % dry/chapped teat skin data.

During trial week 1 with dips containing 0.01 wt. % methylene blue (MB), an average of 10-15% of teats show light blue color prior to premilking teat sanitation at next milking (BP) with 5% emollient dips showing higher results compared to 11% emollient, and minimal to no teat coloration after premilking teat sanitation (AP) or after milking (AM). Teats dipped with products containing 0.02 wt. % MB show a higher percentage of teat coloration BP (40-50%) and 11 wt. % emollient dipped teats show higher coloration AP (25%) and AM (10%). Teats dipped with 0.04 wt. % MB show no coloration advantage to 0.02 wt. % MB. Teats dipped with 0.01 wt. % MB and a thixotropic agent (no drip) show comparable results to 0.02 wt. % MB.

Temperature 5-10 days pretrial is cold (0° F.) followed by 8 days @ 20° F. Then there are 2 days @ 0-5° F., 3 days @ 20° F., then 4 days @ 0° F. (−10° F. minimum temps.) (1$^{st}$ 4 days trial week 2). Trial weeks 3 (40° F.) and 4 (25° F.) are seasonably high for winter.

With respect to teat skin integrity, there is no difference in TE scores and integrity across treatment and control dips and all time periods. 99+% teats showed excellent teat skin health (score 1).

With respect to teat end integrity, control and treatment dipped teats are not significantly different during trial week one (average TE scores or % rough/cracked teats). Control teats have significantly higher TE scores and % rough/cracked TE compared to treatment teats during trial weeks 2-3 (BLB—5% emollient) and trial week 2 (elevated insignificantly in week 3) (NLB—11% emollients); and insignificantly higher in trial week 4. Treatment dipped teats with 5% emollient have more consistent TE results compared to 11% emollient, but caution should be exercised in interpretations as cows were different.

These results show that the test compositions provide some teat coloration at next milking. Furthermore, the test compositions provide excellent teat skin (TS) health as compared to the positive control, excellent teat end health integrity as compared to the positive control, and maintain teat end health integrity through cold weather changes significantly better than controls. Dips with 5 wt. % emollient provide consistent TE health compared, and the test composition dips provide softer, more pliable hyperkeratotic TE tissue than comparative dips.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating or protecting against mastitis in a mammalian teat comprising applying a topical composition to the teat, wherein the topical composition consists essentially of (a) citrate; (b) methylene blue; and (c) an alkyl para-hydroxybenzoate.

2. The method of claim 1, wherein the topical composition comprises:
   (a) about 0.1-2 M citrate;
   (b) about 0.1-3 mM methylene blue; and
   (c) about 10-50 mM alkyl para-hydroxybenzoate.

3. The method of claim 1, wherein the topical composition comprises about 0.005-0.5 wt. % methylene blue.

4. The method of claim 1, wherein the topical composition further comprises about 0.1% to 20% alcohol.

5. The method of claim 1, wherein the topical composition further comprises an emollient.

6. The method of claim 1, wherein the topical composition further comprises anolyte or ascorbic acid.

7. The method of claim 1, wherein the topical composition further comprises sodium at a concentration of about 0.3 M or more.

8. The method of claim 1, wherein the pH of the topical composition is about 4-8.

9. The method of claim 1, wherein the topical composition has a kinimatic viscosity of about 50 cP or more measured at 25° C. and 1 atm pressure.

10. A method of protecting against dryness, chapping, or cracking of the skin of a mammalian teat, the method comprising applying a topical composition to the teat, wherein the topical composition comprises (a) citrate; (b) methylene blue; and (c) alkyl para-hydroxybenzoate.

11. The method of claim 10, wherein the topical composition comprises:
   (a) about 0.1-2 M citrate;
   (b) about 0.1-3 mM methylene blue; and
   (c) about 10-50 mM alkyl para-hydroxybenzoate.

12. The method of claim 10, wherein the topical composition further comprises an emollient.

13. The method of claim 12, wherein the topical composition comprises about 0.005-0.5 wt. % methylene blue.

14. The method of claim 12, wherein the topical composition comprises about 0.1% to 20% alcohol.

15. The method of claim 12, wherein the topical composition further comprises anolyte or ascorbic acid.

16. The method of claim 12, wherein the topical composition further comprises sodium at a concentration of about 0.3 M or more.

17. The method of claim 12, wherein the pH of the topical composition is about 4-8.

18. The method of claim 12, wherein the topical composition has a kinimatic viscosity of about 50 cP or more measured at 25° C. and 1 atm pressure.

19. A method of treating or protecting against mastitis in a mammalian teat comprising applying a topical composition to the teat, wherein the topical composition comprises (a) citrate; (b) methylene blue; (c) an alkyl para-hydroxybenzoate, and, optionally, alcohol, wherein the topical composition is free of any antiseptic or antimicrobial agent other than citrate, methylene blue, alkyl para-hydroxybenzoate, and, optionally, alcohol.

* * * * *